(12) United States Patent
Henning et al.

(10) Patent No.: US 8,946,369 B2
(45) Date of Patent: Feb. 3, 2015

(54) BRANCHED POLYSILOXANES AND USE OF THESE

(71) Applicants: Frauke Henning, Essen (DE); Sadik Amajjahe, Duesseldorf (DE); Ute Linke, Mettmann (DE); Michael Ferenz, Essen (DE); Wilfried Knott, Essen (DE); Volker Arning, Duesseldorf (DE); Bastian Matthias Brugger, Oberhausen (DE); Kathrin Lehmann, Leverkusen (DE)

(72) Inventors: Frauke Henning, Essen (DE); Sadik Amajjahe, Duesseldorf (DE); Ute Linke, Mettmann (DE); Michael Ferenz, Essen (DE); Wilfried Knott, Essen (DE); Volker Arning, Duesseldorf (DE); Bastian Matthias Brugger, Oberhausen (DE); Kathrin Lehmann, Leverkusen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/771,888

(22) Filed: Feb. 20, 2013

(65) Prior Publication Data
US 2013/0217907 A1 Aug. 22, 2013

(30) Foreign Application Priority Data
Feb. 20, 2012 (DE) .......................... 10 2012 202 521

(51) Int. Cl.
  C08G 77/04  (2006.01)
  C08G 77/06  (2006.01)
  C08G 77/08  (2006.01)
  C08G 77/12  (2006.01)
  C08G 77/20  (2006.01)
  C07F 7/08   (2006.01)
  C08L 83/04  (2006.01)
  C08G 77/00  (2006.01)

(52) U.S. Cl.
  CPC .............. *C07F 7/0834* (2013.01); *C08G 77/12* (2013.01); *C08G 77/20* (2013.01); *C08L 83/04* (2013.01); *C08G 77/70* (2013.01)
  USPC .................. 528/10; 528/12; 528/23; 528/31; 528/32; 528/33

(58) Field of Classification Search
  CPC ...... C08G 77/04; C08G 77/045; C08G 77/06; C08G 77/08; C08G 77/10; C08G 77/12; C08G 77/20
  See application file for complete search history.

(56) References Cited

U.S. PATENT DOCUMENTS

| 4,339,564 | A | | 7/1982 | Okamura | |
|---|---|---|---|---|---|
| 4,578,493 | A | | 3/1986 | Chang | |
| 5,162,480 | A | * | 11/1992 | Schilling et al. | 528/23 |
| 5,371,161 | A | | 12/1994 | Knott | |
| 5,430,166 | A | | 7/1995 | Klein | |
| 5,430,167 | A | | 7/1995 | Klein | |
| 5,475,127 | A | | 12/1995 | Klein | |
| 5,698,654 | A | * | 12/1997 | Nye et al. | 528/21 |
| 5,753,751 | A | * | 5/1998 | Liao et al. | 524/837 |
| 5,965,683 | A | * | 10/1999 | Nye et al. | 528/31 |
| 6,127,446 | A | | 10/2000 | Butts | |
| 6,255,511 | B1 | | 7/2001 | Klein | |

(Continued)

FOREIGN PATENT DOCUMENTS

| CA | 2014996 | 11/1990 |
|---|---|---|
| CN | 101899159 A | 12/2010 |

(Continued)

OTHER PUBLICATIONS

English-language equivalent of CN-101899159, 7 pages, 2010.*

*Primary Examiner* — Robert S Loewe
(74) *Attorney, Agent, or Firm* — Scully, Scott, Murphy & Presser, P.C.

(57) ABSTRACT

Branched polysiloxanes of formula (I)

$$M_{a1}M^H_{a2}M^{Vi}_{a3}D_{b1}D^H_{b2}D^{Vi}_{b3}T_{c1}T^H_{c2}T^{Vi}_{c3}Q_d \quad (I)$$

wherein
$M = [R^2R^1_2SiO_{1/2}]$,
$M^H = [R^1_2HSiO_{1/2}]$,
$M^{Vi} = [R^3R^1_2SiO_{1/2}]$,
$D = [R^1_2SiO_{2/2}]$,
$D^H = [R^1HSiO_{2/2}]$,
$D^{Vi} = [R^1R^3SiO_{2/2}]$,
$T = [R^4SiO_{3/2}]$,
$T^H = [HSiO_{3/2}]$,
$T^{Vi} = [R^3SiO_{3/2}]$,
$Q = [SiO_{4/2}]$,
$R^1$ is mutually independently identical or different, linear or branched, saturated or unsaturated hydrocarbon moieties,
$R^2$ is mutually independently the same as $R^1$, an alkoxy moiety or a hydroxy group,
$R^3$ is mutually independently identical or different, linear or branched, olefinically unsaturated hydrocarbon moieties,
$R^4$ is mutually independently $R^1$ or identical or different linear, branched and/or cyclic, saturated or unsaturated hydrocarbon moieties comprising heteroatoms,
a1=from 0 to 50,
a2=from 1 to 50,
a3=from 1 to 50,
b1=from 10 to 5000,
b2=from 0 to 30,
b3=from 0 to 30,
c1=from 0 to 50,
c2=from 0 to 50
c3=from 0 to 50,
d=from 0 to 50,
with the proviso that the sum c1+c2+c3+d is greater than or equal to 1, are provided.

11 Claims, No Drawings

(56) References Cited

U.S. PATENT DOCUMENTS

| | | |
|---|---|---|
| 6,258,913 B1 * | 7/2001 | Herzig et al. .................. 528/15 |
| 6,291,622 B1 | 9/2001 | Dröse |
| 6,307,082 B1 | 10/2001 | Klein |
| 6,376,569 B1 | 4/2002 | Oxman et al. |
| 6,489,498 B2 | 12/2002 | Klein |
| 6,858,663 B2 | 2/2005 | Knott |
| 7,018,458 B2 | 3/2006 | Knott |
| 7,118,619 B2 | 10/2006 | Brandt |
| 7,125,585 B2 | 10/2006 | Dudzik |
| 7,157,541 B2 | 1/2007 | Knott |
| 7,196,153 B2 | 3/2007 | Burkhart |
| 7,241,835 B2 * | 7/2007 | O'Brien et al. .............. 524/862 |
| 7,598,215 B2 | 10/2009 | Hinrichs |
| 7,598,334 B2 | 10/2009 | Ferenz |
| 7,605,284 B2 | 10/2009 | Brueckner |
| 7,612,158 B2 | 11/2009 | Burkhart |
| 7,612,159 B2 | 11/2009 | Burkhart |
| 7,619,035 B2 | 11/2009 | Henning |
| 7,635,581 B2 | 12/2009 | Ferenz |
| 7,645,848 B2 | 1/2010 | Knott |
| 7,727,599 B2 | 6/2010 | Doehler |
| 7,754,778 B2 | 7/2010 | Knott |
| 7,776,989 B2 | 8/2010 | Ferenz |
| 7,825,205 B2 | 11/2010 | Knott |
| 7,825,206 B2 | 11/2010 | Neumann |
| 7,825,207 B2 | 11/2010 | Ferenz |
| 7,825,209 B2 | 11/2010 | Knott |
| 7,834,122 B2 | 11/2010 | Ferenz |
| 7,855,265 B2 | 12/2010 | Thum |
| 7,893,128 B2 | 2/2011 | Busch |
| 7,964,694 B2 | 6/2011 | Ferenz |
| 8,030,366 B2 | 10/2011 | Ferenz |
| 8,138,294 B2 | 3/2012 | Henning |
| 8,172,936 B2 | 5/2012 | Herrwerth |
| 8,198,473 B2 | 6/2012 | Ferenz |
| 8,211,972 B2 | 7/2012 | Meyer |
| 8,247,525 B2 | 8/2012 | Schubert |
| 8,268,939 B2 | 9/2012 | Ebbrecht |
| 8,283,422 B2 | 10/2012 | Schubert |
| 2002/0161158 A1 | 10/2002 | Burkhart |
| 2004/0116640 A1 | 6/2004 | Miyoshi |
| 2006/0081864 A1 * | 4/2006 | Nakazawa .................. 257/98 |
| 2006/0155090 A1 | 7/2006 | Ferenz |
| 2007/0059539 A1 | 3/2007 | Doehler |
| 2007/0128143 A1 | 6/2007 | Gruning |
| 2007/0134424 A1 * | 6/2007 | Tauchi et al. ............. 427/387 |
| 2007/0141739 A1 | 6/2007 | Thompson et al. |
| 2007/0197678 A1 | 8/2007 | Cavaleiro |
| 2007/0199477 A1 | 8/2007 | Hill |
| 2007/0265410 A1 | 11/2007 | Loessel et al. |
| 2008/0125503 A1 | 5/2008 | Henning |
| 2008/0187702 A1 | 8/2008 | Ferenz |
| 2008/0200576 A1 | 8/2008 | Seiler |
| 2009/0137751 A1 | 5/2009 | Knott |
| 2009/0137752 A1 | 5/2009 | Knott |
| 2010/0022435 A1 | 1/2010 | Henning |
| 2010/0029587 A1 | 2/2010 | Brückner |
| 2010/0034765 A1 | 2/2010 | Herrwerth |
| 2010/0036011 A1 | 2/2010 | De Gans |
| 2010/0041910 A1 | 2/2010 | Schubert |
| 2010/0055760 A1 | 3/2010 | Thum |
| 2010/0056649 A1 * | 3/2010 | Henning et al. ............. 521/25 |
| 2010/0071849 A1 | 3/2010 | Knott |
| 2010/0081781 A1 | 4/2010 | Schubert |
| 2010/0105843 A1 | 4/2010 | Knott |
| 2010/0113633 A1 | 5/2010 | Henning |
| 2010/0168367 A1 | 7/2010 | Schubert |
| 2010/0197807 A1 | 8/2010 | Giessler-Blank |
| 2010/0210445 A1 | 8/2010 | von Rymon Lipinski |
| 2010/0248325 A1 | 9/2010 | Eckstein |
| 2010/0249339 A1 | 9/2010 | Henning |
| 2010/0256300 A1 | 10/2010 | Jandke et al. |
| 2010/0266651 A1 | 10/2010 | Czech |
| 2010/0280210 A1 * | 11/2010 | Kitamura et al. ............. 528/31 |
| 2010/0292357 A1 | 11/2010 | Knott |
| 2010/0298455 A1 | 11/2010 | Henning |
| 2011/0021693 A1 | 1/2011 | Henning |
| 2011/0034576 A1 | 2/2011 | Henning |
| 2011/0042004 A1 | 2/2011 | Schubert |
| 2011/0046305 A1 | 2/2011 | Schubert |
| 2011/0070175 A1 | 3/2011 | Herrwerth |
| 2011/0091399 A1 | 4/2011 | Meyer |
| 2011/0172373 A1 | 7/2011 | Knott |
| 2011/0230619 A1 | 9/2011 | Kuppert |
| 2011/0230633 A1 | 9/2011 | Ferenz |
| 2011/0251070 A1 | 10/2011 | Poffenberger |
| 2011/0301254 A1 | 12/2011 | Knott |
| 2011/0306694 A1 | 12/2011 | Glos |
| 2012/0010302 A1 | 1/2012 | Hartung |
| 2012/0027704 A1 | 2/2012 | Henning |
| 2012/0028022 A1 | 2/2012 | Brugger |
| 2012/0029090 A1 | 2/2012 | Brugger |
| 2012/0046486 A1 | 2/2012 | Henning |
| 2012/0067520 A1 | 3/2012 | Schubert |
| 2012/0068110 A1 | 3/2012 | Schubert |
| 2012/0071564 A1 | 3/2012 | de-Gans |
| 2012/0097883 A1 | 4/2012 | Henning |
| 2012/0168664 A1 | 7/2012 | Maurer |
| 2012/0190760 A1 | 7/2012 | Henning |
| 2012/0190762 A1 | 7/2012 | Hubel |

FOREIGN PATENT DOCUMENTS

| | | |
|---|---|---|
| DE | 69019058 T2 | 12/1995 |
| DE | 69122625 T2 | 4/1997 |
| DE | 102009015211 A1 | 10/2010 |
| EP | 0490401 A2 | 6/1992 |
| EP | 1439200 A1 | 7/2004 |
| JP | 201018662 | 1/2010 |
| JP | 201047646 | 3/2010 |
| WO | WO03080753 A1 | 10/2003 |
| WO | WO2006055456 A1 | 5/2006 |
| WO | WO2008036657 | 3/2008 |
| WO | WO2008036662 | 3/2008 |
| WO | WO2009092762 | 7/2009 |
| WO | WO2010049388 | 5/2010 |
| WO | WO2010087523 A1 | 8/2010 |
| WO | WO2010129123 A2 | 11/2010 |

* cited by examiner

US 8,946,369 B2

BRANCHED POLYSILOXANES AND USE OF THESE

FIELD OF THE INVENTION

The invention relates to branched polysiloxanes of formula (I) $M_{a1}M^H_{a2}M^{Vi}_{a3}D_{b1}D^H_{b2}D^{Vi}_{b3}T_{c1}T^H_{c2}T^{Vi}_{c3}Q_d$, and to a process for producing polysiloxanes, in particular those of formula (I). The present invention also relates to use of such polysiloxanes, in particular as, or for producing, curable single-component silicone compositions.

BACKGROUND OF THE INVENTION

Curable silicone compositions are widely used by way of example as sealants and coating materials. Two-component systems composed of a vinyl-functional polysiloxane and of a SiH-functional polysiloxane as a crosslinking agent are very widely used.

The crosslinking reaction takes place through noble-metal-catalyzed hydrosilylation, mostly using platinum complexes. By way of example, U.S. Patent Application Publication No. 2004/0116640 A1 describes a two-component silicone resin composition for producing light-emitting diodes (LEDs) which is hardened thermally after addition of platinum catalysts. Another form of the crosslinking method is light-induced hydrosilylation—also termed photohydrosilylation—and this has been described in many publications including, for example, DE 069019058 T2, DE 069122625 T2, U.S. Pat. No. 6,127,446, WO 2006055456 A1, JP 2010047646 A1 or WO 2009092762 A1. U.S. Patent Application Publication No. 2007/0141739 A1 describes the combination of light-induced and thermally activated hydrosilylation reactions. WO 2010049388 A1 describes a sequential combination of the crosslinking reactions, in that the first step of exposure to light causes insipient crosslinking of the cast silicone part to achieve dimensional stability and a second step cures the entire material thermally.

There are many publications disclosing selected silicone resin formulations constituted from two or more components, where the mechanical, thermal and optical properties of the hardened silicone are adjusted through the proportion of a highly crosslinked resin in the liquid composition, as described by way of example in WO 2010087523 A1, or else by dispersing solid fillers, such as silica, described in JP 2010018662 A1, into the material.

In order to improve adhesion of the sealants and embedding compositions on the substrates and contact areas, it is possible, as described by way of example in U.S. Patent Application Publication No. 2010/0256300 A1 to use alkoxysilanes as adhesion promoters.

A difficulty with the use of multicomponent systems is the stability of the preparation. Partial demixing of incompatible silicones or silanes or precipitation of the solid fillers can cause phase separation and defects in the cured components. The viscosity of formulations of this degree of complexity can also place limits on ease of use if, for example, undesired air inclusions do not escape rapidly. If domains with different crosslinking level are formed during hardening, the resultant variation of mechanical properties leads to an inhomogeneous material with preferential breakage points.

Curable single-component silicone compositions are preferably used in order to avoid the disadvantages described for the multicomponent systems. By way of example, WO 2006/055456 A1 mentions inter alia the use of a single-component silicone resin for producing LEDs through photohydrosilylation.

WO 2008/036662 A1, WO 2008/036657 A1 and EP 0490401 A1 describe linear vinylhydropolysiloxanes and uses of these. DE 102009015211 A1 describes enzyme preparations which are produced with the aid of vinylhydropolysiloxanes, where these can be linear or branched, and can comprise polyether substituents.

U.S. Pat. No. 4,339,564 A1 describes vinylhydropolysiloxanes branched by way of $C_6H_5$—$SiO_{3/2}$ units. In that document, and in U.S. Pat. No. 4,578,493 A1 single-component silicone compositions are also described, where the SiH functions are pendant in the siloxane chain. U.S. Patent Application Publication No. 2007/265410 A1 describes a process for producing single-component silicone compositions of this type through hydrolysis and condensation of chlorosilanes. Contact with aqueous hydrochloric acid liberated during the process degrades some of the pendant SiH groups in the siloxane chain to give SiOH groups, and makes it more difficult to control the level of precrosslinking in the liquid silicone composition.

WO 2010/129123 A1 describes curable single-component silicone compositions having pendant and/or terminal SiH functions and pendant vinyl functions, where these can comprise SiOH groups. The siloxanes are produced through reaction of chlorosilanes in the presence of water. The siloxanes can comprise SiOH groups, and condensation of these produces water, which evaporates slowly and has to be removed by heating in order to achieve complete hardening. The curable single-component silicone compositions described in WO 2010/129123 A1 comprise the majority of the reactive vinyl and SiH functions pendant in the silicone chain.

WO 2003/080753 A1 describes curable single-component silicone compositions which have branching by way of R—$SiO_{3/2}$ units and by way of $SiO_{4/2}$ units and which comprise no $R_2SiO_{2/2}$ units. Very hard materials are obtained, with very low coefficients of thermal expansion. When materials with this level of brittleness are exposed even to low levels of mechanical stress, lack of elasticity can cause hair cracking which reduces the weathering resistance of the material.

In view of the above, there is a need to provide a curable single-component silicone composition which hardens rapidly and homogeneously, preferably adheres well to the substrate and contact areas, and at the same time preferably requires no additional deaerator.

SUMMARY OF THE INVENTION

The present invention provides polysiloxanes of formula (I)

$$M_{a1}M^H_{a2}M^{Vi}_{a3}D_{b1}D^H_{b2}D^{Vi}_{b3}T_{c1}T^H_{c2}T^{Vi}_{c3}Q_d \qquad (I)$$

in which the various variables within formula (I) are as defined below.

The present invention also provides a process for producing polysiloxanes, in particular those of formula (I), and also use of these, in particular as, or for producing, curable single-component silicone compositions.

An advantage of the polysiloxanes according to the invention is that the mechanical properties of the single-component silicone compositions can be adjusted in a controlled fashion through the appropriate selection of the polymer units, without any requirement for mixtures of a plurality of siloxane components.

The polysiloxanes according to the invention and/or the curable single-component silicone compositions produced therefrom exhibit good adhesion to a very wide variety of substrates. Good adhesion here means that rubbing with the tip of a finger on the surface of the hardened silicone does not cause any cracking or any separation from the substrate.

An advantage of the polysiloxanes according to the invention and/or in particular of the curable single-component silicone compositions produced therefrom is low viscosity, ensuring good usage properties, for example, good wetting of the contact areas, good flow into corners which are geometrically difficult to access, and substantial avoidance of gas inclusions, e.g., in casting processes. Complex shapes can therefore be produced without, or almost without, defects.

An advantage of the polysiloxanes according to the invention is that curable single-component silicone compositions produced from the inventive polysiloxanes can be produced without adding deaerators, since gas inclusions can diffuse rapidly out of the low-viscosity silicone composition.

An advantage of the curable single-component silicone compositions produced with the polysiloxanes according to the invention is that the compositions have good mechanical properties in the hardened state, even without filler loading. When the polysiloxanes according to the invention are used, it is possible to omit, to some extent or entirely, the addition of solid, pulverulent fillers, where these require complicated dispersion in the silicone and otherwise frequently promote the formation of gas inclusions, which increases viscosity and thus can impair the catalysis of hardening.

Another advantage of the polysiloxanes according to the invention and/or in particular of the curable single-component silicone compositions produced therefrom is rapid hardening with comparatively small amounts of hydrosilylation catalysts. The low loading with noble-metal catalysts is also advantageous and not only permits the manufacture of colorless components with high optical transparency but also permits the manufacture of components for electronic applications.

Advantages in the use of the polysiloxanes according to the invention and/or in particular of coatings produced from curable single-component silicone compositions are weathering resistance, high thermal stability, low thermal expansion and low susceptibility to yellowing.

Another advantage of the polysiloxanes according to the invention is the possibility of formulating them as a single-component system. An inert catalyst can be added, and can then be activated at the desired juncture by heating or irradiation.

DETAILED DESCRIPTION OF THE INVENTION

The polysiloxanes according to the invention, production of these, and also use of these are described below by way of example, but without any intention that the invention be restricted to these examples. Wherever ranges, general formulae or classes of compounds are given below, these are intended to comprise not only the corresponding ranges or groups of compounds explicitly mentioned but also all of the subranges and subgroups of compounds which can be obtained by extracting individual values (ranges) or compounds. When documents are cited for the purposes of the present description, the entire content of these is intended to become part of the disclosure of the present invention. Where percentages are given below, unless otherwise stated these involve percentages by weight. In the case of compositions, the percentages are based on the entire composition unless otherwise stated. Where average values are given below, unless otherwise stated these involve numeric averages. When measured values are given below, unless otherwise stated these measured values were determined at a pressure of 101325 Pa and at a temperature of 25° C.

A feature of the polysiloxanes according to the invention is that they are polysiloxanes of formula (I)

$$M_{a1}M^H_{a2}M^{Vi}_{a3}D_{b1}D^H_{b2}D^{Vi}_{b3}T_{c1}T^H_{c2}T^{Vi}_{c3}Q_d \qquad (I)$$

where $M=[R^2R^1{}_2SiO_{1/2}]$,
$M^H=[R^1{}_2HSiO_{1/2}]$,
$M^{Vi}=[R^3R^1{}_2SiO_{1/2}]$,
$D=[R^1{}_2SiO_{2/2}]$,
$D^H=[R^1HSiO_{2/2}]$,
$D^{Vi}=[R^1R^3SiO_{2/2}]$,
$T=[R^4SiO_{3/2}]$,
$T^H=[HSiO_{3/2}]$,
$T^{Vi}=[R^3SiO_{3/2}]$,
$Q=[SiO_{4/2}]$, $R^1$ is mutually independently identical or different, linear, branched and/or cyclic, saturated or unsaturated hydrocarbon moieties, preferably aliphatic hydrocarbon moieties having from 1 to 30 carbon atoms or aromatic hydrocarbon moieties having from 6 to 30 carbon atoms, preferably methyl or phenyl, particularly preferably methyl, $R^2$ is mutually independently the same as $R^1$, an alkoxy moiety or a hydroxy group, preferably $R^1$, particularly preferably methyl, $R^3$ is mutually independently identical or different, linear or branched, olefinically unsaturated hydrocarbon moieties, preferably hydrocarbon moieties comprising terminal double bonds, particularly preferably allyl or vinyl, very particularly preferably vinyl, $R^4$ is mutually independently $R^1$ or identical or different linear, branched and/or cyclic, saturated or unsaturated hydrocarbon moieties comprising heteroatoms, preferably oxygen or halogen atoms, preferably haloalkyl, pseudohaloalkyl and carboxyalkyl moieties, particularly preferably 3-chloropropyl, tridecafluoro-1,1,2,2-tetrahydrooctyl, nonafluoro-1,1,2,2-tetrahydrohexyl, 3-acryloxypropyl and 3-methacryloxypropyl, a1=from 0 to 50, preferably <10, with preference 0,
a2=from 1 to 50, preferably from 2 to 30, with preference>=4,
a3=from 1 to 50, preferably from 2 to 30, with preference>=4,
b1=from 10 to 5000, preferably from 10 to 1000, with preference from 10 to 500,
b2=from 0 to 30, preferably from 0 to 12, with preference 0,
b3=from 0 to 30, preferably from 0 to 12, with preference 0,
c1=from 0 to 50, preferably from 1 to 50, with preference>0,
c2=from 0 to 50, preferably from 0 to 50, with preference 0,
c3=from 0 to 50, preferably from 0 to 50, with preference 0,
d=from 0 to 50, preferably from 2 to 20, with preference from 4 to 10,
with the proviso that the sum c1+c2+c3+d is greater than or equal to 1. In some embodiments, it is preferable that d is greater than or equal to 1, with preference from 4 to 10, c1=c2=c3 being 0.

The polysiloxanes of the formula (I) can be composed of the various monomer units in blocks one on top of another, with any desired number of blocks and with any desired sequence, or can have a random distribution of the various monomer units. The indices used in the formulae are to be considered as statistical average values.

The ratio of the sum a2+b2+c2 to the sum a3+b3+c3 in the polysiloxanes according to the invention is preferably from 1:10 to 10:1, with preference from 1:5 to 5:1 and with particular preference in particular from 1:2 to 2:1. It is preferable that the sum a2+b2+c2 is preferably the same as or smaller than the sum a3+b3+c3.

In one embodiment of the present invention, b1>b2 and b1>b3, in particular b1>b2+b3. In another embodiment of the present invention, b2=0, b3=0 and b 1>c1+c2+c3+d. In still yet another embodiment of the present invention, b2, b3, c1, c2 and c3 are equal to 0 and b1>d.

The polysiloxanes according to the invention and having formula (I) are preferably liquid at a temperature of 25° C. and at a pressure of 101325 Pa. The viscosity of the polysiloxanes according to the invention and having formula (I) is preferably smaller than 450 mPa*s, measured at 25° C. by a method based on DIN 5391 with a Brookfield (LVT) Synchro-Lectric rotary viscometer and LV 2 spindle.

The polysiloxanes according to the invention and having formula (I) can be produced by any possible method known to the person skilled in the art. The polysiloxanes according to the invention are preferably produced in accordance with the process according to the invention and described below.

The process according to the invention for producing branched polysiloxanes having olefinically unsaturated groups and having SiH groups, preferably polysiloxanes according to the invention and having formula (I) as defined above, features the following components:
a) one or more silanes or siloxanes which have one or more SiH functions and which have no olefinically unsaturated hydrocarbon moieties, and
b) optionally one or more SiH function-free siloxanes which have no olefinically unsaturated hydrocarbon moieties, and
c) one or more silanes or siloxanes which have one or more olefinically unsaturated hydrocarbon moieties, and
d) one or more tetraalkoxysilanes, and/or
e) one or more trialkoxysilanes, which do not have any SiH functions or vinyl functions, where all of the silanes which are used for components a), c), d) and e) have alkoxy groups, preferably methoxy or ethoxy groups,
are reacted with addition of water and in the presence of at least one Brönstedt-acid catalyst. In one embodiment of the present invention, the Brönstedt-acid catalyst is selected from the sulphonic acids or from compounds having sulphonic acid groups.

In some embodiments, the molar amounts used of components a) to e) are selected in such a way as to give polysiloxanes of formula (I. The molar ratio of the $M^{Vi}$ units used in the form of the starting materials to the $M^H$ units used in the form of the starting materials is preferably from 1:0.8 to 1:4, with preference from 1:1 to 1:3, with particular preference from 1:1 to 1:2 and with very particular preference 1:1. It is preferable that the components used are not components which comprise $D^H$ units and $D^{Vi}$ units. Accordingly, component a) is preferably a dimethylhydroalkoxysilane, dihydrotetramethyldisiloxane or α,ω-dihydropolydimethylsiloxane and component c) is preferably a dimethylvinylalkoxysilane, divinyltetramethyldisiloxane or α,ω-divinylpolydimethylsiloxane. The molar ratio of branching T or Q units to chain-terminating M units, where the ratio is selected by way of amounts used of components a) to e), is preferably from 0.25:1 to 25:1, with preference from 0.3:1 to 3:1, with particular preference from 0.5:1 to 1:1. The molar ratio of the entirety of M units, T units and Q units to the chain-extending D units, where the ratio is defined by way of the amounts used of components a) to e), is preferably from 1:1 to 1:500, with preference from 1:1 to 1:250.

The Brönstedt-acid catalyst is preferably a Brönstedt-acid catalyst which is solid at 25° C. and 1013 mbar, preferably being one selected from acidic ion-exchanger resins having sulphonic acid groups.

Brönstedt-acid catalysts used can be ion exchangers or ion-exchanger resins known from the prior art. The process according to the invention can use not only natural ion exchangers, for example, zeolites, montmorillonites, attapulgites, bentonites and other aluminium silicates, but also synthetic ion exchangers. The latter are preferably solids (mostly granular) with a three-dimensional high-molecular-weight matrix which is insoluble in water and is based on phenol-formaldehyde resins, or are copolymers of styrene-divinylbenzene into which numerous "anchor" groups of differing acidity have been incorporated. Particular materials that can be used are acidic aluminas or acidic ion-exchanger resins, for example the products with the known trademarks Amberlite®, Amberlyst® or Dowex® and Lewatit®. In some embodiments, it is particularly preferable to use a sulphonic-acid ion-exchanger resin as acidic ion exchanger.

Acidic ion exchangers used in the process according to the invention are preferably those of the type described in EP 1 439 200. The aforementioned document and the documents cited as prior art therein are hereby incorporated by way of reference and are part of the disclosure of the present invention.

It can be advantageous for the process according to the invention to use, as a catalyst, at least one solid acidic ion exchanger (catalyst 1) and at least one other, non-solid Brönstedt-acid catalyst (catalyst 2), in particular a liquid acid. A mineral acid can be used as catalyst 2 here, preferably sulphuric acid and/or preferably an organic sulphonic acid, preferably trifluoromethanesulphonic acid. The catalyst mixture is preferably added directly to the reaction mixture. In some embodiments, it is preferable to use, as a catalyst, a mixture of trifluoromethanesulphonic acid and of a sulphonic-acid ion-exchanger resin, preferably Lewatit® K 2621 (Bayer Material Science). It is preferable that the ratio by mass of catalyst 1 to catalyst 2 in the catalyst mixture is from 10:1 to 100:1. The ratio by mass is in particular preferred when a Lewatit® catalyst is used as catalyst 1 and trifluoromethanesulphonic acid is used as catalyst 2.

The process according to the invention preferably completely omits solvents which are not miscible with water in equal parts by weight without phase separation. In particular, the process according to the invention does not use any alkanes or aromatic compounds as solvents.

It can be advantageous for the process according to the invention to use water or a mixture of water and of one or more organic solvents miscible with water in equal parts by weight without phase separation. This method can achieve better compatibilization and thus better mixing of the water with the siloxanes and/or silanes. However, in another possible method of achieving good mixing, the water is added with particularly good mechanical mixing, or is introduced into the mixture of silanes and of siloxanes in the form of a vapor, e.g., by bubbling steam into the mixture.

Organic solvents which can be used and are miscible in equal parts by weight with water without phase separation (standard conditions) can preferably be alcohols, in particular alcohols having from 1 to 6 carbon atoms, with preference given to monohydric alcohols and with particular preference given to methanol or ethanol, in particular ethanol. The amount of the solvent added is preferably sufficiently large as to give a reaction mixture in which some or all of the water has been homogenized. If a mixture of water and of an appropriate solvent, for example, ethanol is used, the ratio by weight of water to solvent in the mixture is preferably from 1:1 to 10:1, preferably from 2:1 to 5:1.

Component a)

SiH-functional silanes used can by way of example comprise dimethylmonoalkoxysilanes, methyldialkoxysilanes or trialkoxysilanes. Siloxanes used and having one or more SiH functions can by way of example be those in which the arrangement of the SiH functions in the siloxane is purely terminal, purely pendant, or mixed terminal and pendant. SiH-functional siloxanes used can by way of example comprise linear polymethylhydrosiloxanes, for example, HMS-993 from Gelest Inc., linear polydimethylmethylhydrosiloxanes, for example, HMS-031 and/or HMS-071 from Gelest Inc., linear α,ω-dihydropolydimethylsiloxanes, for example, 1,1,3,3-tetramethyldisiloxane and/or 1,1,3,3,5,5-hexamethyltrisiloxane, relatively high-molecular-weight oligomers, for example, DMS-H03 and/or DMS-H11 from Gelest Inc., cyclic polymethylhydrosiloxanes, for example, tetramethylcyclotetrasiloxane or pentamethylcyclopentasiloxane and cyclic polydimethylmethylhydrosiloxanes, for example, heptamethylcyclotetrasiloxane and/or nonamethylcyclopentasiloxane, or a mixture thereof. SiH-functional siloxanes used particularly preferably comprise 1,1,3,3-tetramethyldisiloxane, DMS-H03, HMS-993 (in each case from Gelest Inc.) and pentamethylcyclopentasiloxane.

Component b)

SiH-function-free siloxanes that can be used comprise by way of example linear polydimethylsiloxanes, for example, hexamethyldisiloxane or cyclic polydimethylsiloxanes, for example, octamethylcyclotetrasiloxane and/or decamethylcyclopentasiloxane. In some embodiments, it is preferable to use hexamethyldisiloxane and decamethylcyclopentasiloxane.

Component c)

Silanes and siloxanes used which comprise at least one olefinically unsaturated hydrocarbon moiety preferably comprise those which comprise at least one undecenyl, allyl or vinyl moiety. Silanes or siloxanes as component c) are preferably selected from the allyltrialkoxysilanes, e.g., allyltrimethoxysilane or allyltriethoxysilane, allyldialkoxysilanes, e.g., allyldimethoxysilane, allylmethyldimethoxysilane, allyldiethoxysilane or allylmethyldiethoxysilane, allylmonoalkoxysilanes, undecenyltrialkoxysilanes, e.g., undecenyltrimethoxysilane, vinyltrialkoxysilanes, e.g., vinyltrimethoxysilane, vinyltriethoxysilane, vinyltriisopropoxysilane or vinyltributoxysilane, vinyldialkoxysilanes, e.g., vinyldimethoxysilane, vinylmethyldimethoxysilane, vinylphenyldimethoxysilane vinyldiethoxysilane, vinylmethyldiethoxysilane, vinylphenyldiethoxysilane, and vinylmonoalkoxysilanes, e.g., vinylphenylmethylmethoxysilane, allyloxy-undecyltrimethoxysilane, 1,3-diallyltetramethyldisiloxane, vinyltriacetoxysilane, 1,3-divinyltetramethyldisiloxane, vinyltetramethyldisiloxane and 1,3-divinyltetraphenyldisiloxane.

Component d)

Tetraalkoxysilanes used can in principle comprise any of the tetraalkoxysilanes, in particular tetramethoxysilane, tetraethoxysilane or tetraisopropoxysilane or condensates of these. Tetraalkoxysilanes used can comprise those in which the alkoxy moieties are all identical, all different or to some extent identical. In some embodiments, it is particularly preferable to use tetraethoxysilane.

Component e)

Trialkoxysilanes used can in principle comprise any of the trialkoxysilanes which differ from component a) and c). Trialkoxysilanes used can in particular comprise those in which the alkoxy moieties are all identical, all different or to some extent identical. Trialkoxylsilanes used can in particular comprise those which differ from component a) and c). In some embodiments, it is particularly preferable to use triethoxysilanes, preferably alkyltriethoxysilanes, for example, methyltriethoxysilane, ethyltriethoxysilane, n-propyltriethoxysilane, isobutyltriethoxysilane, pentyltriethoxysilane, hexyltriethoxysilane, octyltriethoxysilane, hexadecyltriethoxysilane, n-octadecyltriethoxysilane, halogen-containing or pseudohalogen-containing alkyltrialkoxysilane, in particular halogen-containing or pseudohalogen-containing alkyltriethoxysilanes, for example, chloropropyltriethoxysilane, tridecafluoro-1,1,2,2-tetrahydrooctyltriethoxysilane, nonafluoro-1,1,2,2-tetrahydrohexyltriethoxysilane, 3-cyanopropyltriethoxysilane, trialkoxysilanes, in particular triethoxysilanes with functional groups, for example 3-acryloxypropyltriethoxysilane, 3-methacryloxypropyltriethoxysilane, 5-(bicycloheptenyl)triethoxysilane, phenyltriethoxysilane, (p-chloromethyl)phenyltriethoxysilane, or dihydro-3-[3-(triethoxysilyl)propyl]furan-2, 5-dione. It can be advantageous to use organically functionalized trialkoxysilanes as branching unit (to include these in the equilibrium). Preferred trialkoxysilanes are methyltriethoxysilane and phenyltriethoxysilane.

In some cases, it can be advantageous to use one or more tetraalkoxysilanes and one or more trialkoxysilanes in the process according to the invention. However, it is preferable to use one or more tetraalkoxysilanes (component d)) and no trialkoxysilanes (component c)).

The process according to the invention preferably uses exclusively components a) to e) which are liquid under standard conditions (25° C., 1013 mbar).

The process according to the invention can react the components in the presence of the catalyst(s) in one step. The process according to the invention is preferably carried out in a multistage, preferably two-stage, process. Irrespective of the number of stages, it can be advantageous for the components to be added sequentially. This applies in particular to the multistage, preferably two-stage, process.

A reaction mixture can be obtained by any desired mixing of the components. It is possible either to mix all of the components involved, and react these, or to begin by mixing at only some of the components, and reacting these, and reacting the reaction product with one or more further components.

It is preferable that at least one Brönstedt-acid catalyst is added after the mixing of the components. Some or all of the catalyst can be added directly to the reaction mixture, or the catalyst can be metered into the reaction in any desired sequence.

It is preferable to begin by mixing the components, and then to add the catalyst and then to add the water or an aqueous mixture.

If the catalyst used comprises the two catalysts 1 and 2, it can be advantageous to begin by adding catalyst 2, preferably in its entirety, to the mixture of the components, and then to add the water, and to add catalyst 1 only after water, preferably the entirety thereof, has been added. However, it is also possible to add both of the catalysts 1 and 2 to the components prior to addition of the water.

If the production process according to the invention is carried out in a two-stage process, it can be advantageous to use catalyst 2 with or without catalyst 1 in the first step, using components a), c), d) and/or e) and water, and only catalyst 2 in the second step, using one or more of components a) to c), preferably using components a) and b).

The amount of Brönstedt-acid catalyst added to the reaction mixture in the process according to the invention is preferably such that the entirety of the Brönstedt-acid catalysts used is from 0.01 to 10% by weight, based on the total weight of components a) to e) used. Particular subranges within the range can be preferred, depending on the nature and concentration of the catalyst used. By way of example, particular preference is given to the use of amounts of from 0.05% by weight to 0.5% by weight of trifluoromethanesulphonic acid. If an ion-exchanger resin is used alone as catalyst, the weight of catalysts used is preferably from 3 to 10% by weight. If the catalyst used comprises a combination of mineral acid and/or organic sulphonic acids with an ion-exchanger resin, the weight of ion-exchanger resin used is preferably from 3 to 6% by weight, based on the total weight of components a) to e) used.

The process according to the invention preferably uses from 0.5 to 30 mol of water per mole of alkoxysilane used. Hydrolysis and condensation preferably use from 1 to 6 mol of water per mole of alkoxysilane. The water can be added in one step, or preferably metered into the mixture over a prolonged period. The amount of water selected usually results in no phase separation.

The reaction in the process according to the invention is preferably carried out at a temperature of from 0° C. to 100° C., preferably from 20° C. to 60° C.

Once the reaction has been terminated, the volatile by-products of condensation can be removed, for example by vacuum distillation under mild conditions. If necessary or desired, neutralization can be carried out, for example with a basic salt, preferably with sodium hydrogencarbonate.

The polysiloxanes according to the invention and having the formula (I), or the polysiloxanes produced according to the invention, can by way of example be used as, or for producing, curable (single-component) silicone compositions.

These curable silicone compositions according to the invention, in particular single-component silicone compositions, which comprise polysiloxanes according to the invention and having the formula (I) or which comprise polysiloxanes produced according to the invention can comprise further constituents, for example, constituents which adjust, or can affect, chemical or physical properties. By way of example, the silicone compositions according to the invention can comprise particles for modifying rheological or optical properties, for example, fine-particle silica (Aerosil) for adjusting rheological properties, such as thixotropy or pseudoplasticity, particles for altering refractive index, e.g., titanium dioxide, or phosphorus components for spectral alteration from fluorescence effects. The silicone compositions according to the invention can comprise by way of example the following constituents which can affect thermal expansion, thermal conductivity or electrical conductivity: electrically or thermally conductive substances, for example, metals, for example, silver, nickel, copper or gold, or by way of example oxides, for example, indium tin oxide or zinc oxide.

The curable silicone compositions according to the invention can be used as sealing and adhesive preparations, coating compositions and encapsulating and embedding compositions, or can be sealing and adhesive preparations, coating compositions and encapsulating and embedding compositions.

The curable silicone compositions according to the invention can be formulated with the hydrosilylation catalysts of the prior art, for example, platinum catalysts, which can be activated thermally or by UV radiation. Platinum catalysts active at room temperature can usually, as in the prior art, be modified by adding inhibitors.

The invention further provides hardened compositions produced using the polysiloxanes according to the invention and having the formula (I) or using the polysiloxanes produced according to the invention. These hardened compositions can by way of example be foils, electronic, optical and optoelectronic components, composite products and semifinished products. The properties of the said hardened compositions are affected by the constitution of the polysiloxanes according to the invention and having the formula (I) and the aggregates described above.

Test Method(s):

The person skilled in the art knows how to record and interpret the NMR spectra. A reference which may be introduced here is the book "NMR Spectra of Polymers and Polymer Additives" by A. Brandolini and D. Hills, published in 2000 by Verlag Marcel Dekker Inc. Viscosities were determined by a method based on DIN 5391 with a Brookfield (LVT) Synchro-Lectric rotary viscometer and LV 2 spindle.

The subject matter of the present invention is explained in more detail below by using examples, but there is no intention to restrict the subject matter of the invention to the said exemplary embodiments. The molecular formulae mentioned in the headings of the synthesis examples correspond to theoretical constitution derived from the respective weights of the starting materials.

EXAMPLES

Example 1

Production of Olefinically Unsaturated SiH-Functional Polysiloxanes of the Formula $M^{Vi}_6 M^H_6 D_{21} Q_5$ 198.7 g of an alpha, omega-dihydropolydimethylsiloxane with SiH-value 3.0 eq of SiH/kg, 55.9 g of divinyltetramethyldisiloxane (ABCR, 96%) and 104.0 g of tetraethoxysilane (Sigma Aldrich, 98%) were used as initial charge at 40° C., with stirring, in a four-necked flask equipped with a stirrer with precision glass gland, an internal thermometer, a dropping funnel and a distillation bridge, and 0.206 ml of trifluoromethanesulphonic acid (obtainable from Sigma Aldrich) was added and the mixture was stirred for two hours. Within 20 minutes, a mixture of 18 g of deionized water and 4.5 g of ethanol was added dropwise, with stirring, and the mixture was stirred for a further two hours. Alcohol and excess water were then removed by distillation in the vacuum provided by a water pump, about 12 mbar, for three hours at from 40° C. to 50° C. The mixture was neutralized with 7 g of sodium hydrogencarbonate and filtered. This gave a clear, colorless liquid with viscosity 10 mPa*s at room temperature and hydrogen content 1.9 eq of SiH/kg (89.6% of theory). The ratio of M units to D units calculated from the $^{29}$Si NMR spectrum was 1:1.91. This gives a molecular formula $M^{Vi}_6 M^H_{5.3} D_{21.7} Q_5$.

Example 2

Production of Olefinically Unsaturated SiH Functional Polysiloxanes of the Formula $M^{Vi}_6 M^H_{5.7} D_{87} Q_5$ 102.2 g of decamethylcyclopentasiloxane (obtainable from Gelest Inc.), 3.63 g of alpha,omega-dihydropolydimethylsiloxane with SiH value 3.0 eq of SiH/kg and 60 g of the siloxane produced in example 1 were used as initial charge at 40° C., with stirring, in a four-necked flask equipped with a stirrer with precision glass gland, an internal thermometer, a dropping funnel and a distillation bridge. After addition of 9.9 g of predried sulphonic-acid cation-exchanger resin Lewatit® K 2621 (10% by weight water content—determined by a method based on the Karl Fischer method), the mixture was stirred at 40° C. for six hours. The resin was removed by filtration and the product was distilled for two hours at 130° C. and 12 mbar. The residue obtained was a clear, colorless liquid with viscosity 90 mPa*s at room temperature and hydrogen content 0.5 eq of SiH/kg (66% of theory). The ratio of M units to D units calculated from the $^{29}$Si NMR spectrum was 1:7.3.

Example 3

Production of Olefinically Unsaturated SiH-Functional Polysiloxanes of the Formula $M^{Vi}_6M^H_{5.8}D_{142}Q_5$ 124.6 g of decamethylcyclopentasiloxane (obtainable from Gelest Inc.), 2.43 g of alpha,omega-dihydropolydimethylsiloxane with SiH value 3.0 eq of SiH/kg and 40 g of the siloxane produced in example 1 were used as initial charge at 40° C., with stirring, in a four-necked flask equipped with a stirrer with precision glass gland, an internal thermometer, a dropping funnel and a distillation bridge. After addition of 10 g of predried sulphonic-acid cation-exchanger resin Lewatit® K 2621 (10% by weight water content—determined by a method based on the Karl Fischer method), the mixture was stirred at 40° C. for six hours. The resin was removed by filtration and the product was distilled for two hours at 130° C. and 12 mbar. The residue obtained was a clear, colorless liquid with viscosity 45 mPa*s at room temperature and hydrogen content 0.41 eq of SiH/kg (82% of theory). The ratio of M units to D units calculated from the $^{29}$Si NMR spectrum was 1:12.9.

Example 4

Production of Olefinically Unsaturated SiH-Functional Polysiloxanes of the Formula $M^{Vi}_6M^H_6D_{196}Q_5$ 135.6 g of decamethylcyclopentasiloxane (obtainable from Gelest Inc.), 2.43 g of alpha,omega-dihydropolydimethylsiloxane with SiH value 3.0 eq of SiH/kg and 30 g of the siloxane produced in example 1 were used as initial charge at 40° C., with stirring, in a four-necked flask equipped with a stirrer with precision glass gland, an internal thermometer, a dropping funnel and a distillation bridge. After addition of 10 g of predried sulphonic-acid cation-exchanger resin Lewatit® K 2621 (10% by weight water content—determined by a method based on the Karl Fischer method), the mixture was stirred at 40° C. for six hours. The resin was removed by filtration and the product was distilled for two hours at 130° C. and from 10 to 15 mbar. The residue obtained was a clear, colorless liquid with viscosity 181 mPa*s at room temperature and hydrogen content 0.28 eq of SiH/kg (75% of theory). The ratio of M units to D units calculated from the $^{29}$Si NMR spectrum was 1:23.

Examples 1 to 4 show that low-viscosity liquids, i.e., liquids with viscosity smaller than 450 mPa*s at 23° C., are always obtained.

Comparative Examples

Example 5

Comparative Example 1 for Producing Olefinically Unsaturated SiH-Functional Polysiloxanes of the Formula $M^H_2D^{Vi}_{22}D^H_{43}$ from WO 2010/129123

5.23 g of dihydrotetramethyldisiloxane (obtainable from ABCR), 73.8 g of tetramethyltetravinylcyclotetrasiloxane (obtaintable from ABCR), and 100 g of tetrahydrotetramethylcyclotetrasiloxane were used as initial charge at room temperature, with stirring, in a three-necked flask equipped with a stirrer with precision glass gland, an internal thermometer, and a nitrogen valve, 0.179 g of trifluoromethanesulphonic acid (obtainable from Sigma Aldrich) were added, and the mixture was stirred for six hours. 3.6 g of sodium hydrogencarbonate were then added, and the mixture was stirred at room temperature overnight. The mixture was then neutralized for a further six hours at 60° C., and filtered. This gave a clear, colorless liquid with viscosity 38 mPa*s at room temperature and hydrogen content of 9.72 eq of SiH/kg. The ratio of M units to D units calculated from the $^{29}$Si NMR spectrum was 1:32.

Example 6

Comparative Example 2 for Producing Olefinically Unsaturated SiH-Functional Polysiloxanes of the Formula $M^H_4D_{302}T^{Vi}_2$ 8.78 g of an alpha,omega-dihydropolydimethylsiloxane with SiH value 3.0 eq of SiH/kg, 150 g decamethylpentasiloxane (obtainable from Gelest Inc.) and 0.16 g of trifluoromethanesulphonic acid (obtainable from Sigma Aldrich) were used as initial charge at room temperature, with stirring, in a four-necked flask equipped with a stirrer with precision glass gland, an internal thermometer, a dropping funnel and a distillation bridge. 2.76 g of vinyltriethoxysilane (Evonik Industries) were then added, and the mixture was stirred at 40° C. for two hours. A mixture of 0.4 g of deionized water and 0.01 g of ethanol was then added dropwise, with stirring, and the mixture was stirred at 45° C. for a further two hours. Alcohol and excess water were then removed by distillation in a rotary evaporator at about 1 mbar, for two hours at from 40° C. to 50° C. The mixture was neutralized with 3.2 g of sodium hydrogen carbonate and filtered. Finally, excess decamethylpentasiloxane was removed on a rotary evaporator at 110° C. and 1 mbar. This gave a clear, colorless liquid with viscosity 488 mPa*s at room temperature and hydrogen content 0.14 eq of SiH/kg. The ratio of M units to D units calculated from the $^{29}$Si NMR spectrum was 1:85.

Example 7

Comparative Example 3 for Producing Olefinically Unsaturated SiH-Functional Polysiloxanes of the Formula $M_2D_{9.1}D^{Vi}_{7.0}D^{Ph}_{16.7}{}^H$ 6.48 g of hexamethyldisiloxane (obtaintable from Fluka), 31 g of tetramethyltetravinyltetrasiloxane (obtaintable from ABCR), 39.84 g of tetrahydrotetramethyltetrasiloxane (obtainable from ABCR) and 0.14 g of trifluoromethanesulphonic acid (obtainable from Sigma Aldrich) were used as initial charge at room temperature, with stirring, in a four-necked flask equipped with a stirrer with precision glass gland, an internal thermometer, a dropping funnel and a distillation bridge. 54.69 g of methylphenyldiethoxysilane (obtainable from ABCR) were then added, and the mixture was stirred at 40° C. for two hours. A mixture of 2.3 g of deionized water and 0.58 g of ethanol was then added dropwise, with stirring, and the mixture was stirred at 45° C. for a further two hours. Alcohol and excess water were then removed by distillation in a rotary evaporator at about 1 mbar, for two hours at from 40° C. to 50° C. The mixture was neutralized with 2.6 g of sodium hydrogencarbonate and filtered. Finally, excess was removed on a rotary evaporator at 110° C. and 1 mbar.

This gave a clear, colorless liquid with viscosity 13 mPa*s at room temperature and hydrogen content 4.5 eq of SiH/kg (89.6% of theory).

Use as Coating and Casting Composition

Example 8

Formulation Example F1

10 g of the vinylhydrosiloxane produced in example 1 were mixed with 0.3 g of a solution of a platinum(0)-divinyltetramethyldisiloxane complex in decamethylcyclopentasiloxane at a concentration of 0.1% by weight of platinum (obtainable from Umicore with 21.37% by weight of platinum, adjusted to 0.1% by weight of Pt by dilution with decamethylcyclopentasiloxane). After the mixing process, the mixture cured within ten minutes at room temperature. The curing time was the time required for the mixture to be tack-free. When the surface of the cured silicone is touched by the tip of the finger, a cured silicone feels smooth and no longer feels tacky or liquid.

Example 9

Formulation Example F2

The material is formulated as in example 5, except that the product from example 2 was used instead of the product from example 1. After the mixing process, the mixture cures at room temperature within five minutes.

Example 10

Formulation Example F3

The material is formulated as in example 5, except that the product from example 3 was used instead of the product from example 1. After the mixing process, the mixture cures at room temperature within two minutes.

Example 11

Formulation Example F4

The material is formulated as in example 5, except that the product from example 4 was used instead of the product from example 1. After the mixing process, the mixture cures at room temperature within two minutes.

Example 12

Formulation Example F5

10 g of the vinylhydrosiloxane produced in example 4 are mixed with 0.02 g of a solution of the platinum(0)-divinyltetramethyldisiloxane complex in decamethylcyclopentasiloxane at a concentration of 0.1% by weight of platinum. After the mixing process, the mixture cures at room temperature within two minutes.

Example 13

Formulation Example F6

The material is formulated as in example 1, except that the product from example 5 (comparative example 1) was used instead of the product from example 1. After the mixing process, the mixture does not harden, even after 24 hours. When the temperature of the material is controlled to 80° C., curing occurs after five minutes.

Example 14

Formulation Example F7

The material is formulated as in example 1, except that the product from example 6 (comparative example 2) was used instead of the product from example 1. After the mixing process, the mixture does not harden either at room temperature or at 80° C. within 24 hours.

Example 15

Formulation Example F8

The material is formulated as in example 1, except that the product from example 7 (comparative example 3) was used instead of the product from example 1. After the mixing process, the mixture does not harden, even after 24 hours. When the temperature of the material is controlled to 80° C., curing occurs after 10 minutes.

Examples 8 to 12 show that the branched vinylhydrosiloxanes according to the invention permit very rapid hardening at room temperature. In particular example 12 provides evidence of the rapid hardening at very low catalyst concentrations.

Example 16

Hardening Example H1

Using a method based on DIN 53504, dumbbell specimens with prescribed dimensions were cast with the mixture from example 8 and hardened at 80° C. for 10 minutes.

Example 17

Hardening Example H2

Using a method based on DIN 53504, dumbbell specimens with prescribed dimensions were cast with the mixture from example 9 and hardened at 80° C. for 10 minutes.

Example 18

Hardening Example H3

Using a method based on DIN 53504, dumbbell specimens with prescribed dimensions were cast with the mixture from example 10 and hardened at room temperature for 10 minutes.

Example 19

Hardening Example H4

Using a method based on DIN 53504, dumbbell specimens with prescribed dimensions were cast with the mixture from example 11 and hardened at room temperature for 10 minutes.

Example 20

Determination of Rheological Properties

Using a method based on DIN 53504 the rheological properties listed in table 1 were determined for hardening examples H1, H2, H3 and H4 (examples 10 to 13) with a universal tester, using a roller tensioning system with tensioning rate 200 mm/min Tensile strength is defined as the maximum tensile force reached immediately prior to onset fracture of the material. Tensile strain at break is defined as the maximum length increase reached at the juncture, based on initial length.

TABLE 1

Results of tests according to example 20

| Hardening example | Tensile strength/MPa | Tensile strain at break/% |
|---|---|---|
| H1 | 0.45 | 7 |
| H2 | 0.42 | 27 |
| H3 | 0.2 | 29 |
| H4 | 0.34 | 54 |

Example 21

Determination of Thermal Stability

Each of formulation examples F1 and F5 was hardened in a round aluminium dish to give a layer of thickness 1.5 mm. The dishes were aged in a drying oven at 200° C. for three days. No shrinkage or cracking was observed. To evaluate yellowing, the layer was separated from the aluminium substrate and assessed visually by comparison on a white background. Hardened formulation example F5 exhibited no yellowing, while slight yellowing was visible in the case of hardened formulation example F1.

Example 22

Determination of Optical Transmittance

To determine optical transmittance, formulation example F1 and F3, but with 0.02 g of a solution of the platinum(0)-divinyltetramethyldisiloxane complex in decamethylcyclopentasiloxane at a concentration of 0.1% by weight of platinum, were transferred to UV cells and cured at room temperature. Transmittance was then measured by using a UV spectrometer from Helios Zeta in the wavelength range from 200 to 900 nm. Transmittance was >92% in the wavelength range from 300 to 900 nm for both specimens.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:
1. A polysiloxane of formula (I)

$$M_{a1}M^{H}{}_{a2}M^{Vi}{}_{a3}D_{b1}D^{H}{}_{b2}D^{Vi}{}_{b3}T_{c1}T^{H}{}_{c2}T^{Vi}{}_{c3}Q_{d} \quad (I)$$

wherein
$M=[R^2R^1{}_2SiO_{1/2}]$,
$M^H=[R^1{}_2HSiO_{1/2}]$,
$M^{Vi}=[R^3R^1{}_2SiO_{1/2}]$,
$D=[R^1{}_2SiO_{2/2}]$,
$D^H=[R^1HSiO_{2/2}]$,
$D^{Vi}=[R^1R^3SiO_{2/2}]$,
$T=[R^4SiO_{3/2}]$,
$T^H=[HSiO_{3/2}]$,
$T^{Vi}=[R^3SiO_{3/2}]$,
$Q=[SiO_{4/2}]$,
$R^1$ is mutually independently identical or different, linear or branched, saturated or unsaturated hydrocarbon moieties,
$R^2$ is mutually independently the same as $R^1$, an alkoxy moiety or a hydroxy group,
$R^3$ is mutually independently identical or different, linear or branched, olefinically unsaturated hydrocarbon moieties comprising terminal bonds,
$R^4$ is mutually independently $R^1$ or identical or different linear, branched and/or cyclic, saturated or unsaturated hydrocarbon moieties comprising heteroatoms,
a1=from 0 to 50,
a2=from 1 to 50,
a3=from 1 to 50,
b1=from 10 to 5000,
b2=from 0 to 30,
b3=from 0 to 30,
c1=from 0 to 50,
c2=from 0 to 50,
c3=from 0 to 50,
d=from 4 to 10.
2. A polysiloxane according to claim 1, wherein c1=c2=c3=0.
3. A polysiloxane according to claim 1, wherein a ratio of the sum of a2, b2 and c2 to the sum of a3, b3 and c3 is from 1:10 to 10:1.
4. A polysiloxane according to claim 1, wherein b2=0, b3=0 and b1>c1+c2+c3+d.
5. A process for producing branched polysiloxanes having olefinically unsaturated groups and having SiH groups, comprising reacting
one or more silanes or siloxanes which have one or more SiH functions and which have no olefinically unsaturated hydrocarbon moieties,
one or more silanes or siloxanes which have one or more olefinically unsaturated hydrocarbon moieties, one or more SiH function-free siloxanes having no olefinically unsaturated hydrocarbon moieties,
one or more tetraalkoxysilanes, and/or
one or more trialkoxysilanes,
where all of the silanes used for each of said components have alkoxy groups, with addition of water and in the presence of at least one Brönstedt-acid catalyst, and wherein said branched polysiloxanes are of formula (I)

$$M_{a1}M^{H}{}_{a2}M^{Vi}{}_{a3}D_{b1}D^{H}{}_{b2}D^{Vi}{}_{b3}T_{c1}T^{H}{}_{c2}T^{Vi}{}_{c3}Q_{d} \quad (I)$$

wherein
$M=[R^2R^1{}_2SiO_{1/2}]$,
$M^H=[R^1{}_2HSiO_{1/2}]$,
$M^{Vi}=[R^3R^1{}_2SiO_{1/2}]$,
$D=[R^1{}_2SiO_{2/2}]$,
$D^H=[R^1HSiO_{2/2}]$,
$D^{Vi}=[R^1R^3SiO_{2/2}]$,
$T=[R^4SiO_{3/2}]$,
$T^H=[HSiO_{3/2}]$,
$T^{Vi}=[R^3SiO_{3/2}]$,
$Q=[SiO_{4/2}]$,
$R^1$ is mutually independently identical or different, linear or branched, saturated or unsaturated hydrocarbon moieties,
$R^2$ is mutually independently the same as $R^1$, an alkoxy moiety or a hydroxy group,
$R^3$ is mutually independently identical or different, linear or branched, olefinically unsaturated hydrocarbon moieties comprising terminal bonds, $R^4$ is mutually independently $R^1$ or identical or different linear, branched and/or cyclic, saturated or unsaturated hydrocarbon moieties comprising heteroatoms, a1=from 0 to 50,
a2=from 1 to 50,
a3=from 1 to 50,
b1=from 10 to 5000,
b2=from 0 to 30,
b3=from 0 to 30,
c1=from 0 to 50,
c2=from 0 to 50,
c3=from 0 to 50,
d=from 4 to 10.

6. The process according to claim 5, wherein said Brönstedt-acid catalyst comprises an acidic ion-exchanger resin which has sulphonic acid groups and which is solid at 25° C. and 1013 mbar.

7. A curable single-component silicone composition comprising at least a polysiloxane of formula (I)

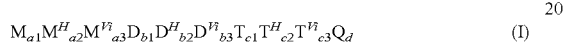
(I)

wherein
$M=[R^2R^1{}_2SiO_{1/2}]$,
$M^H=[R^1{}_2HSiO_{1/2}]$,
$M^{Vi}=[R^3{}_R{}^1{}_2SiO_{1/2}]$,
$D=[R^1{}_2SiO_{2/2}]$,
$D^H=[R^1HSiO_{2/2}]$,
$D^{Vi}=[R^1R^3SiO_{2/2}]$,
$T=[R^4SiO_{3/2}]$,
$T^H=[HSiO_{3/2}]$,
$T^{Vi}=[R^3SiO_{3/2}]$,
$Q=[SiO_{4/2}]$, $R^1$ is mutually independently identical or different, linear or branched, saturated or unsaturated hydrocarbon moieties, $R^2$ is mutually independently the same as $R^1$, an alkoxy moiety or a hydroxy group, $R^3$ is mutually independently identical or different, linear or branched, olefinically unsaturated hydrocarbon moieties comprising terminal bonds, $R^4$ is mutually independently $R^1$ or identical or different linear, branched and/or cyclic, saturated or unsaturated hydrocarbon moieties comprising heteroatoms, a1=from 0 to 50,
a2=from 1 to 50,
a3=from 1 to 50,
b1=from 10 to 5000,
b2=from 0 to 30,
b3=from 0 to 30,
c1=from 0 to 50,
c2=from 0 to 50,
c3=from 0 to 50,
d=from 4 to 10.

8. The silicone composition according to claim 7, wherein c1=c2=c3=0.

9. The silicone composition according to claim 7, wherein a ratio of the sum of a2, b2 and c2 to the sum of a3, b3 and c3 is from 1:10 to 10:1.

10. The silicone composition according to claim 7, wherein b2=0, b3=0 and b1>c1+c2+c3+d.

11. The silicone composition according to claim 7, further comprising additional constituents which adjust or affect chemical and/or physical properties.

* * * * *